US008911782B2

(12) United States Patent
Harriton et al.

(10) Patent No.: US 8,911,782 B2
(45) Date of Patent: Dec. 16, 2014

(54) TRANSDERMAL PATCHES HAVING IONIZED BEAM CROSSLINKED POLYMERS AND IMPROVED RELEASE CHARACTERISTICS

(75) Inventors: Matthew Harriton, New York, NY (US); Gregory Robb, Lawrence, NJ (US); Ronald S. Harland, Yardley, PA (US)

(73) Assignee: Specialty Pharmaceutical Products LLC, Tullytown, PA (US)

( * ) Notice: Subject to any disclaimer, the term of this patent is extended or adjusted under 35 U.S.C. 154(b) by 0 days.

(21) Appl. No.: 13/444,348

(22) Filed: Apr. 11, 2012

(65) Prior Publication Data

US 2013/0078299 A1  Mar. 28, 2013

Related U.S. Application Data

(60) Provisional application No. 61/473,992, filed on Apr. 11, 2011, provisional application No. 61/481,449, filed on May 2, 2011.

(51) Int. Cl.
| | |
|---|---|
| *A61K 9/14* | (2006.01) |
| *A61K 31/167* | (2006.01) |
| *A61K 9/06* | (2006.01) |
| *A61K 9/70* | (2006.01) |
| *A61K 47/36* | (2006.01) |
| *A61K 47/10* | (2006.01) |
| *A61K 47/32* | (2006.01) |

(52) U.S. Cl.
CPC .............. *A61K 47/10* (2013.01); *A61K 31/167* (2013.01); *A61K 9/06* (2013.01); *A61K 9/7053* (2013.01); *A61K 47/36* (2013.01); *A61K 9/70* (2013.01); *A61K 47/32* (2013.01)
USPC ......................................................... 424/484

(58) Field of Classification Search
None
See application file for complete search history.

(56) References Cited

U.S. PATENT DOCUMENTS

| | | | | |
|---|---|---|---|---|
| 4,750,482 | A | * | 6/1988 | Sieverding .................... 604/317 |
| 2002/0026005 | A1 | | 2/2002 | Munro |
| 2003/0170308 | A1 | * | 9/2003 | Cleary et al. .................. 424/486 |
| 2004/0242770 | A1 | | 12/2004 | Feldstein et al. |

(Continued)

OTHER PUBLICATIONS

Kacarevic-Popovic et al, On the Use of Radiation Technology for Nanoscale Engineering of Silver/Hydrogel Based Nanocomposites for Potential Biomedical Application, The Open Conference Proceedings Journal, 2010, vol. 1, pp. 200-206.*

(Continued)

*Primary Examiner* — Paul Dickinson
(74) *Attorney, Agent, or Firm* — Beck & Thomas, P.C.

(57) ABSTRACT

Crosslinked hydrogel-based transdermal pharmaceutical formulations. The hydrogel transdermal formulations. Transdermal patches are useful for administering a variety of drugs to patients. The transdermal patches here employ crosslinked-hydrogels generated through irradiation, thus eliminating any residual effects associated with chemical- or UV-based crosslinking procedures. The transdermal patches may be formed from a variety of high-molecular weight polymeric compounds and include substantial levels of water to improve skin tolerance by the patient. The transdermal patches may also include transcutol as a solvent for the drug, which has been found to increase the effectiveness of drug delivery. The present disclosure also provides for methods of loading a drug into a transdermal formulation after the crosslinking of the hydrogel, thus improving stability and bioavailability through avoiding exposure of the drug to the radiation used in the crosslinking procedure. The transdermal patches here are particularly effective in delivering lidocaine to patients in need thereof.

12 Claims, 4 Drawing Sheets

(56) References Cited

U.S. PATENT DOCUMENTS

2005/0112151 A1   5/2005   Horng
2008/0292684 A1   11/2008  Colombo et al.
2009/0053290 A1*  2/2009   Sand et al. .................... 424/449
2009/0258060 A1   10/2009  Cleary et al.
2012/0214874 A1   8/2012   Buyuktimkin et al.

OTHER PUBLICATIONS

International Searching Authority, Notification of Transmittal of the International Search Report and the Written Opinion of the International Searching Authority, or the Declaration for Application No. PCT/US2012/033071, Jul. 11, 2012.

* cited by examiner

TRANSDERMAL PATCHES HAVING IONIZED BEAM CROSSLINKED POLYMERS AND IMPROVED RELEASE CHARACTERISTICS

CROSS-REFERENCE TO RELATED APPLICATIONS

This application claims the benefit under 35 U.S.C. §119 (e) of the earlier filing date of U.S. Provisional Patent Application No. 61/473,992 filed on Apr. 11, 2011 and U.S. Provisional Patent Application No. 61/481,449 filed on May 2, 2011.

BACKGROUND OF THE INVENTION

1. Field of the Invention

This application discloses inventions that relate generally and in various embodiments to transdermal patches useful for delivering various medicaments to patients in need thereof.

2. Description of the Background

Transdermal drug delivery systems have become an increasingly important means of administering medicaments to patients. Such systems offer advantages over other modes of administration such as, for example, introduction through ingestion via the gastro-intestinal tract or through injections.

Transdermal patches generally include a reservoir comprised of a hydrogel containing the medicament. Hydrogels are formed from very long molecular chain polymers that are crosslinked, and contain water. Such crosslinked water soluble polymers may be used as effective reservoirs as they provide a comfortable and conformable interface with the skin, as well as excellent biocompatibility. Additional hydrogels may also be used to promote healing in wound dressings. See U.S. Pat. No. 5,578,661, which is hereby incorporated by reference.

Hydrogels used in the pharmaceutical industry generally come in two basic forms—amorphous gel and sheet gel. While amorphous gels are useful as lotions to spread on the skin, transdermal patches typically employ sheet gels in their formulation and construction. To formulate a hydrogel as a sheet, some form of chemical crosslinking is typically employed. Crosslinking is essentially a process by which the polymers that make up the hydrogel are covalently crosslinked to one another, thereby providing physical structure to the gel.

Common methods of crosslinking include UV-induced crosslinking and chemical crosslinking. By mixing the polymeric hydrogel composition with specific chemical crosslinking agents, crosslinks between the polymers are formed. The chemical crosslinking agent remains in the hydrogel and, as such, the crosslinking process continues to occur at a slow rate during the storage of the transdermal patch depending on ambient temperature, humidity, or other environmental factors. Furthermore, the chemical crosslinking agent that remains in the transdermal patch may chemically interfere either directly or with the absorption into the skin of certain active agents, thereby attenuating the effectiveness of the transdermal patch. With UV-induced crosslinking, the crosslinking is achieved by controlled exposure to UV light without the use of chemicals. UV-induced crosslinking may also continue after the initial treatment with UV light through subsequent exposure of the transdermal patch to sunlight. Thus, for both chemical and UV-induced crosslinking, the art has encountered difficulties in achieving precise control of the crosslinking process and thus the generation of a consistent transdermal product.

In contrast to chemical or UV-induced crosslinking, crosslinking through electron beam or ionized beam radiation provides numerous benefits. Such techniques are disclosed in U.S. Pat. No. 4,684,558, which is hereby incorporated by reference. Ionized beam crosslinking occurs when the hydrogel is exposed to an accelerated, high-energy beam of electrons, thereby causing crosslinking among the polymeric strands. The first benefit is that ionized beam crosslinked hydrogels possess an improved purity of formulation, given no additional chemical components need to be added, as in chemical crosslinking. Furthermore, because the crosslinking occurs only when the gel is exposed to the high-energy electron beam, the ability to reproducibly generate patches having the same characteristics is dramatically improved.

The use of electron beam or ionized beam radiation in crosslinking may, however, generate a complication for drug-containing hydrogels. Commonly, an unformed reservoir is incorporated with a biologically active agent (i.e., a drug) before the ionization or curing process begins. This drastically limits the choice of drug to only those that are stable during the crosslinking process. The high-energy particles may degrade the drug and the products of that degradation reaction can interfere with both the crosslinking reaction as well as the efficacy of the formulation.

To avoid these concerns, some procedures in the prior art allow the patient to add a separate drug-containing phase to a transdermal patch at the time of use. This process is not only cumbersome for the patient, but also gives rise to significant issues of compliance and formulation variability. The prior art does not provide an effective manner for generating a drug-containing crosslinked hydrogel transdermal formulations that avoids these complications.

Hydrogels that are able to be crosslinked through irradiation may be formulated from a diversity of compounds. Those include the water-soluble polymers include irradiated crosslinked polyethylene oxide (PEO), polyvinyl pyrrolidone (PVP), polyvinyl alcohol (PVA), polyacrylamide, and polyethylene glycol (PEG). The crosslinked water soluble polymer sheet by nature of its preparation by irradiation crosslinking is of low bioburden and is non-toxic, non-irritating and non-sensitizing to the skin. This is particularly assured by the fact that no chemical crosslinking agents or organic solvents are required to synthesize the crosslinked water soluble polymer material.

While these physical characteristics of ionized beam crosslinked hydrogel sheets are known in the prior art, the impact that these factors may have on transdermal patch performance have yet to be investigated.

Additionally, transdermal formulations are often augmented by various compounds to improve either physical or physiological properties, though it is unknown how such compounds impact the bioavailability or stability of biologically active components in a crosslinked hydrogel. One such additive is transcutol, also known as 2-(2-ethyoxethoxy)ethanol, carbitol, carbitol cellosolve, dioxitol, poly-solv DE, and dowanal DE; (hereinafter "transcutol"). Transcutol is a clear, colorless, hygroscopic liquid and is commonly used as an industrial solvent. As a solvent, it is able to transfer various polar and non-polar medicaments (i.e., drugs) into a solid or semisolid substrate for administration to patients. The use of transcutol as a skin penetration enhancer is known, though the impact it may have on drug-containing hydrogel stability and delivery of drugs from a hydrogel transdermal patch is unexplored. See U.S. Pat. No. 5,460,620, which is hereby incorporated by reference.

SUMMARY OF THE INVENTION

The present invention provides crosslinked hydrogels useful for generating transdermal pharmaceutical formulations.

The hydrogel transdermal formulations of the present invention may be formed from a variety of polymers that are able to crosslinked through irradiation. When formed into transdermal patches, the hydrogels of the present invention may also include the compound transcutol which has been found to improve the effectiveness of drug delivery. The present invention further provides a method of loading a biologically active component (i.e., medicament or drug) into the hydrogel-based transdermal formulations after the crosslinking of the hydrogel. This process provides improvement in the stability and bioavailability of the pharmaceutical formulation by avoiding exposure of the drug to the radiation used in crosslinking.

In some embodiments, an object of the present invention is to provide a pharmaceutical preparation for external application to the skin containing lidocaine which comprises a drug-retaining layer, wherein said drug-retaining layer comprises a hydrogel base and 1 to 10% by weight of lidocaine, said base comprising a water-soluble high molecular weight substance, water, and transcutol as a solvent. In some embodiments, the hydrogel may also include a water-retaining agent such as polyethylene glycol.

An object of the present invention is thus to provide a transdermal formulation for administering a medicament to a patient in need thereof, that includes a hydrogel formulated from a polymer-water mixture and transcutol, wherein said hydrogel is generated by exposing said polymer-water mixture to ionizing radiation and a medicament dispersed in said hydrogel. In some embodiments the medicament is lidocaine. The transdermal patches of the present invention delivers two to four times more lidocaine to said patient over a twelve-hour period than LIDODERM®. In some embodiments, the polymer used in the hydrogel may be polyethylene oxide, polyvinylpyrrolidone, polyethylene glycol, or mixtures thereof. The polymer may be present at a concentration of about 3% to about 60% and water may be present from about 1% to about 90%. The patches may also include a water-retaining agent at a concentration from about 1% to about 70%. The water-retaining agent may be a glycol, a saccharide, including ethylene glycol, diethylene glycol, polyethylene glycol, glycerin, sorbitol, martitol, propylene glycol, or 1,3-butylene glycol. The transdermal formulations of the present invention may have a pH from about 5.0 to about 7.8. In some embodiments, the transdermal formulation possesses a polymer-water mixture comprises about 22% polyvinylpyrrolidone, about 27% polyethylene glycol, and about 50% deionized water and between about 0.5% and about 20% medicament.

Another object of the present invention is a method of loading a hydrogel transdermal patch with a medicament, comprising the steps of formulating a hydrogel, wherein said hydrogel comprises a high-molecular weight polymer, water, and transcutol; exposing said hydrogel to ionizing radiation; and contacting said hydrogel with a solution containing said medicament after said exposing step. In certain embodiments the medicament is lidocaine that is absorbed into a fabric as the solution. The drug is loaded into the hydrogel through the woven or nonwoven fabric.

A further object of the present invention is an external preparation for application to the skin containing lidocaine which comprises a drug-retaining layer placed on a support, wherein said drug-retaining layer comprises an hydrogel base and 1 to 10% by weight of lidocaine, said hydrogel base comprising 0.5 to 50% by weight of a water-soluble high molecular weight compound, 30 to 70% by weight of water, and 1 to 70% by weight of transcutol, said lidocaine being dissolved in the base so as to result in a uniform base material. The water-soluble high molecular weight compounds may be selected from the group consisting of selected from the group consisting of gelatin, starch, agar, mannan, alginic acid, polyacrylic acid, a salt of polyacrylic acid, dextrin, methylcellulose, methylcellulose sodium, carboxymethylcellulose, carboxymethylcellulose sodium, polyvinyl alcohol, polyvinyl pyrrolidone, copolymer of methyl vinyl ether and maleic anhydride, gum arabic, tragacanth, karaya gum and locust bean gum.

BRIEF DESCRIPTION OF THE DRAWINGS

Various embodiments of the invention are described herein in by way of example in conjunction with the following figure.

DETAILED DESCRIPTION OF THE INVENTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

The present invention provides for hydrogel-based transdermal formulations that may be used to deliver a wide variety of biological active compounds to a patient in need thereof. In certain embodiments, the transdermal formulation is a transdermal patch formed from a hydrogel that has been crosslinked through irradiation. In some embodiments, the transdermal patch may also include transcutol which improves the skin penetration of the drug and maintains the tacky properties of the transdermal patch. Additionally, the present invention also provides methods for loading hydrogel-based transdermal patches with drug after the hydrogel is crosslinked by radiation, thus avoiding exposure of the drug to the radiation. The post-loading process results in an improved bioavailability of the drug and prolonged effectiveness of the formulations.

Transdermal patches of the present invention may be formed from hydrogel sheets irradiated in the following manner. An electron beam accelerant is used to generate a source of electrons. Those electrons are then passed through an electron gun which discharges those electrons through a series of magnetic fields. Each time the electrons pass through a magnetic field, they accelerate, and eventually a very high speed electron is produced. Using additional magnets, that electron beam is focused into a beam of smaller area, some embodiments having a size of approximately 1 square inch. That beam is swung rapidly back and forth using magnets creating a curtain of electrons. In some embodiments, the beam of electrons is swept across the hydrogel surface at approximately 200 times per second at a 36" wide span. The hydrogel sheet may be exposed to irradiating beam for varying lengths of time or varying dosages of radiation as determined by the properties the user wishes the formulation to possess given the particular polymer-water mixture that is employed in the transdermal formulation. In some embodiments, the hydrogel is exposed to a range of radiation from about 0.5 megarads to about 12 megarads.

The hydrogels of the present invention may be formulated by mixing a water-soluble polymer such as polyethylene oxide, polyvinylpyrrolidone, polyethylene glycol, or mixtures thereof with water to create a polymer-water mixture. Other high-molecular weight compounds that may be used in the context of the present invention include polyvinyl alcohol (PVA), polyacrylamide, gelatin, starch, agar, mannan, alginic acid, polyacrylic acid, a salt of polyacrylic acid, dextrin, methylcellulose, methylcellulose sodium, carboxymethylcellulose, carboxymethylcellulose sodium, copolymer of methyl vinyl ether and maleic anhydride, gum arabic, tragacanth, karaya gum and locust bean gum.

The polymer concentration in the polymer-water mixture ranges from about 3% to about 60% by weight with the remainder of the composition being water. Water contained in the hydrogel base increases the swelling of the skin horny layer and the permeability of the drug. The water concentration may vary from about 10% to about 90%, with 20% to 50% being particularly effective. The thickness of the hydrogel may also vary widely, with 25 mil for the non-loaded hydrogel being particularly effective.

The polymer-water mixture becomes very viscous and may be subsequently coated onto a backing material, mesh, or similar material. In other embodiments, the backing material, mesh, or the like need not be used and the polymer-water mixture may be rolled or spread onto a flat surface alone. The spread polymer-water mixture is then exposed to the oscillating ionizing radiation beam as described above. When the electrons hit the polymers, the electrons break some of the links between the polymers and a free radical is formed through the release of a hydrogen atom. That creates an opening in the carbon chain of the polymer and allows a carbon atom in one polymeric chain to bond to a carbon atom from another polymer chain thereby creating crosslinks between the polymeric strands and extending polymer lengths.

By employing ionizing beam radiation to crosslink the hydrogel, the percentage of crosslinking may be tightly controlled. The percentage of crosslinking impacts how much water the hydrogel is able to retain. In that manner, the percentage of crosslinking may control the tackiness of the hydrogel. Thus, the present invention provides new methods for producing novel transdermal patches where the degree of crosslinking and water content may be manipulated consistently over a wide range. For example, some of the hydrogels of the present invention do not contain any adhesive, but instead rely only on the high water content of the hydrogel to adhere to the skin. As such, there need not be any adhesive bonding of the hydrogel to the skin or the hair, and accordingly, there is not as much interference with the surface of the skin and skin irritation is thereby reduced. Additionally, the transdermal patch may be removed without the painful ripping out of hair so often associated with the use of common adhesive formulations. Indeed, in some circumstances the high water content of the hydrogels of the present invention may be skin palliative and support healing of skin. Further, because of the lack of additional chemical agents (e.g., chemical crosslinking agents), the likelihood for skin irritation may be reduced.

The hydrogel-containing transdermal patches of the present invention may also include transcutol, acting as a solvent for the drug. The amount of transcutol in the hydrogel base may range from about 1 to about 70%, with 10 to 60% being particularly effective. The transcutol may be added prior to the polymer-water mixture prior to irradiation or may be introduced as a solvent/carrier for the drug as it is loaded into the preformed hydrogel.

In some embodiments, the hydrogel may also include a water-retaining agent. The water-retaining agent includes, for example, glycols or saccharides such as ethylene glycol, diethylene glycol, polyethylene glycol, glycerin, sorbitol, martitol, propylene glycol, 1,3-butylene glycol, and similar compounds. One or more water-retaining agent may be used. An amount of the water-retaining agent in the adhesive gel base may be in a range of about 1 to about 70%, with 10 to 60% being particularly effective. In still other embodiments, no water-retaining agent is present. In those formulations, the drug, a water-soluble high-molecular weight substance, water, and transcutol would be present in the hydrogel.

A particularly useful formulation of the transdermal patches of the present possesses the following components:
22% polyvinyl pyrrolidone
27% polyethylene glycol 300
0.50% phenoxyethanol
0.18% methylparaben
0.05 propylparaben
50.27% deionized water The transdermal patch formulations of the present invention are particularly effective in delivering lidocaine to patients. Lidocaine-containing transdermal patches may possess the following formulations. Variations in concentration of each component are well tolerated within the context of the present invention, thus the following examples are not limiting. Furthermore, combinations of transcutol and propylene glycol may be used where the relative concentration of each component may be varied freely from 0-100%, with formulation 3 providing one such example.

| Formulation 1 | Formulation 2 | Formulation 3 |
|---|---|---|
| 16.69% lidocaine (free base) | 16.69% lidocaine (free base) | 16.69% lidocaine (free base) |
| 82.86% transcutol | | 8.29% transcutol |
| | 82.86% propylene glycol | 74.57% propylene glycol |
| 0.30% phenoxyethanol | 0.30% phenoxyethanol | 0.30% phenoxyethanol |
| 0.1% methylparaben | 0.1% methylparaben | 0.1% methylparaben |
| 0.05% propylparaben | 0.05% propylparaben | 0.05% propylparaben |

If necessary, there can also be used a conventional absorbing agent such as salicylic acid, hyaluronic acid, oleic acids N,N-diethyl-m-toluamide, n-butyl stearate, benzyl alcohol, isopropyl myristate, isopropyl palmitate, polypropylene glycol, crotamiton, diethyl sebacate, N-methylpyrrolidone, N-ethylpyrrolidone, lauryl alcohol, etc., and a surfactant for emulsifying the absorbing agent in the gel base, including, for example, polyoxyethylene sorbitan monooleate, polyoxyethylene sorbitan monostearate, sorbitan monooleate, and sorbitan monopalmitate. In addition, a preserving agent (e.g., parabens), an antioxidant (e.g., ascorbic acid, vitamin E), or other compound designed to improve stability of the formulation (e.g., EDTA, DTPA, and derivatives thereof) may also be used in a suitable amount. Any kind and amount of antioxidant or preserving agent may be used unless they negatively affect on the control release of the drug or irritate the skin.

The hydrogel base comprising the above components may have a pH of 5 to 9 in view of the stimuli to the skin and the stability of the drug. The pH may be adjusted to the above range by adding an alkaline substance such as sodium hydroxide or an amine such as triethanolamine or diisopropanolamine or an acid substance such as hydrochloric acid, tartaric acid, citric acid, malic acid, lactic acid, acetic acid, phthalic acid, or other physiologically acceptable acid. The transdermal patch may have a pH ranging from about 5.0 to about 7.8. The pH of the final transdermal patch product may be adjusted either before or after the drug has been added. One of skill in the art will recognize that the timing of pH adjustment may be chosen to accommodate the particular properties and stability of the drug being loaded.

The transdermal sheet hydrogels of the present invention may be loaded with numerous physiologically active agents. Medicaments which penetrate the skin may be utilized in the context of the present invention. Examples of drugs that can be used with the hydrogels of the present invention include analgesics (e.g., fentanyl, buprenorphine), anesthetics (e.g., lidocaine), antianginals (e.g., calcium channel blockers, nitroglycerin), antifungals, antibiotics, anticancer drugs, antiinflammatories, anthelmintics, antidotes, antiemetics (e.g., scopolamine), antihistamines, antihypertensives, antimalarials, antimigraine agents, antimicrobials, antipsychotics, antipyretics, antiseptics, antiarthritics, antithrombin agents, antituberculotics, antitussives, antivirals, steroids (e.g., birth control formulations of estrogen), antismoking agents (e.g., nicotine), appetite suppressants, cardioactive drugs, cathartics, chemotherapeutic agents, coronary, cerebral, or peripheral vasodilators, contraceptive agents, antidepressants (e.g., selegiline), depressants, diagnostic aids, diuretics, expectorants, hormonal agents, hypnotics, immunosuppression agents, narcotic antagonists, parasympathomimetics, sedatives, stimulants (e.g., methylphenidrate), sympathomimetics, vitamins (e.g., vitamin B12), tranquilizers, urinary antiinfectives, and vasoconstrictors. In sum, the hydrogel-based patches of the present invention may be used with any compound that may be effectively delivered transdermally. In some embodiments, the drug is lidocaine.

When employing anesthetics and/or analgesics, the compositions and methods of the present invention can be used to treat or prevent any indication resulting from noxious stimulation of peripheral nociceptors. The compositions and methods of the invention are effective to induce local anesthesia and to treat neuropathic pain. As used herein the term "neuropathic pain" refers to neuropathic-pain syndromes, that is, pain due to lesions or dysfunction in the nervous system. The compositions and methods of the invention can be used to treat or prevent pain related to or induced by the following diseases, trauma, or conditions: general neuropathic conditions, such as peripheral neuropathy, phantom pain, reflex-sympathetic dystrophy, causalgia, syringomyelia, and painful scar; specific neuralgias at any location of the body; back pain; diabetic neuropathy; alcoholic neuropathy; metabolic neuropathy; inflammatory neuropathy; chemotherapy-induced neuropathy, herpetic neuralgias; traumatic odontalgia; endodontic odontalgia; thoracic-outlet syndrome; cervical, thoracic, or lumbar radiculopathies with nerve compression; cancer with nerve invasion; traumatic-avulsion injuries; mastectomy, thoracotomy pain; spinal-cord-injury; stroke; abdominal-cutaneous nerve entrapments; tumors of neural tissues; arachnoiditis; stump pain; fibromyalgia; regional sprains or strains; myofascial pain; psoriatic arthropathy; polyarteritis nodosa; osteomyelitis; burns involving nerve damage; AIDS-related pain syndromes; connective tissue disorders, such as systemic lupus erythematosis, systemic sclerosis, polymyositis, and dermatomyositis; and inflammatory conditions, such as acute inflammation (e.g., trauma, surgery and infection) or chronic inflammation (e.g., arthritis and gout).

The external preparation for application to the skin containing lidocaine of the invention can be prepared by adding the drug (e.g., lidocaine or a pharmaceutically acceptable salt thereof such as lidocaine hydrochloride) in an effective amount to the above-described hydrogel base to prepare a drug-retaining layer, the content of the drug being in a range of 0.5 to 20.0%, with 2.5 to 10.0% being particularly effective.

In order to protect the drug-retaining layer from the volatilization of water and from wear and tear during use, a liner made of a suitable material may also be adhered to the surface of said layer prior to use. The liner may be placed on the surface of the transdermal patch that is to be applied to the patient's skin. The transdermal patch may also include a support on the rear of the hydrogel (i.e., the portion not facing the skin of the patient). The support may be made of a flexible material which is capable of fitting in the movement of human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and similar compounds or structures.

In certain embodiments, the hydrogel base includes only a water-soluble high molecular weight compound, water, lidocaine, and transcutol. In such embodiments, the adherent properties of the hydrogels of the present invention may decrease. To promote contact between the transdermal patches of the present invention and the patient a so-called island patch construction may be used. In an island patch construction, the central portion of the transdermal patch is the drug-containing hydrogel described above. Around the edges of the transdermal patch, there may be a small perimeter (e.g., $3/8^{th}$ of an inch) of adhesive that would seal the hydrogel to the skin. This formulation has the added benefit of not allowing the water in the patch to evaporate during use by the patient.

The hydrogel-based transdermal patches may be loaded with drug in the following manner. The manufacturing procedure of the present invention includes methods of loading a hydrogel patch with an amount of a biologically active agent that meets the FDA requirements of assay and product uniformity. This manufacturing procedure also yields drug concentration uniformity on finished product. Prior art transdermal products typically have the drug premixed with the reservoir which is then cured to form a semi-solid material which is usually adhesive. This adhesive gel is laminated onto a backing liner or support and then cured. See, e.g., U.S. Pat. No. 5,741,510, which is hereby incorporated by reference.

The present invention also encompasses methods of manufacturing a transdermal product by post-loading the hydrogel with a biologically active agent that may be dissolved in a skin-friendly solvent, e.g. transcutol. In some embodiments, the solvent may be a mixture of multiple ingredients in which the drug is soluble. The formulation preferably does not result in phase separation of either the drug or any other component of the hydrogel composition, thus providing a uniform formulation for application to the skin. The present inventive methods promote the ability of the crosslinked hydrogel to absorb large quantities of solvent, while retaining appropriate strength, adhesion and tack in the swollen state. Peppas, N, Hydrogels in Medicine and Pharmacy, Vol. I, CRC Press (1986); Bueche, F. Physical Properties of Polymers, Chapter 2, Interscience, New York (1962); Charlesby, A. Atomic Radiation and Polymers, Pergamon Press (1960), which are hereby incorporated by reference.

For purposes of ease of manufacture and obtaining product with concentration and content uniformity as well as physiological effectiveness, the hydrogel acts as a transdermal drug reservoir and is able to absorb several hundred percent of its own weight in drug-loaded solvent to obtain an effective amount of the biologically active agent.

In certain embodiments, dropping and/or smearing the drug solution on the surface of the hydrogel is effective to load the biologically active agent into the hydrogel. The solution containing the drug should be applied onto the surface of the hydrogel without splashing, missing the reservoir altogether, or having solution run off as this will compromise the content uniformity of the final transdermal patch product and result in wasted drug solution.

Figure 1:
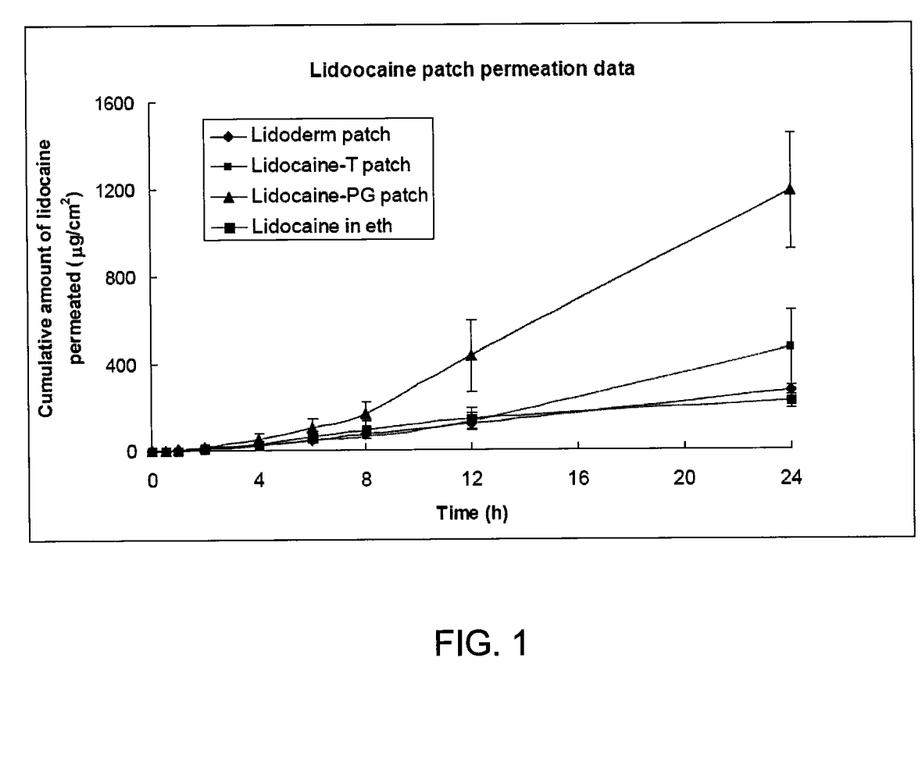
FIG. 1 shows the cumulative amount of lidocaine released by transdermal patch formulations of the present invention and Lidoderm®.
Figure 2:
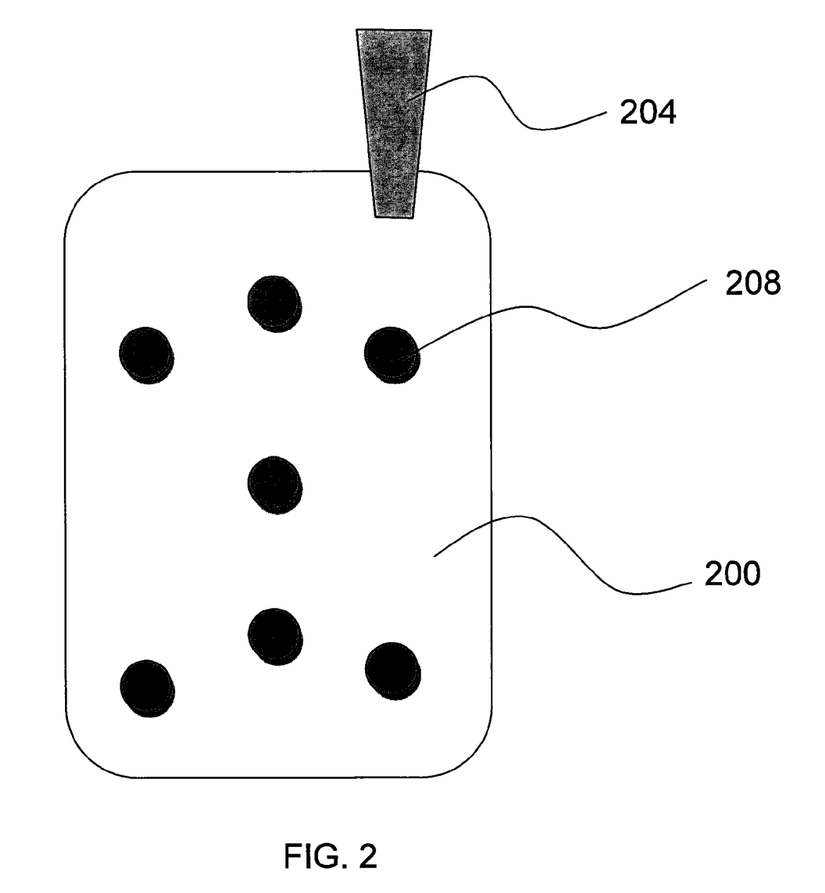
FIG. 2 displays one manner of post-loading the hydrogel formulations of the present invention.
Figure 3:
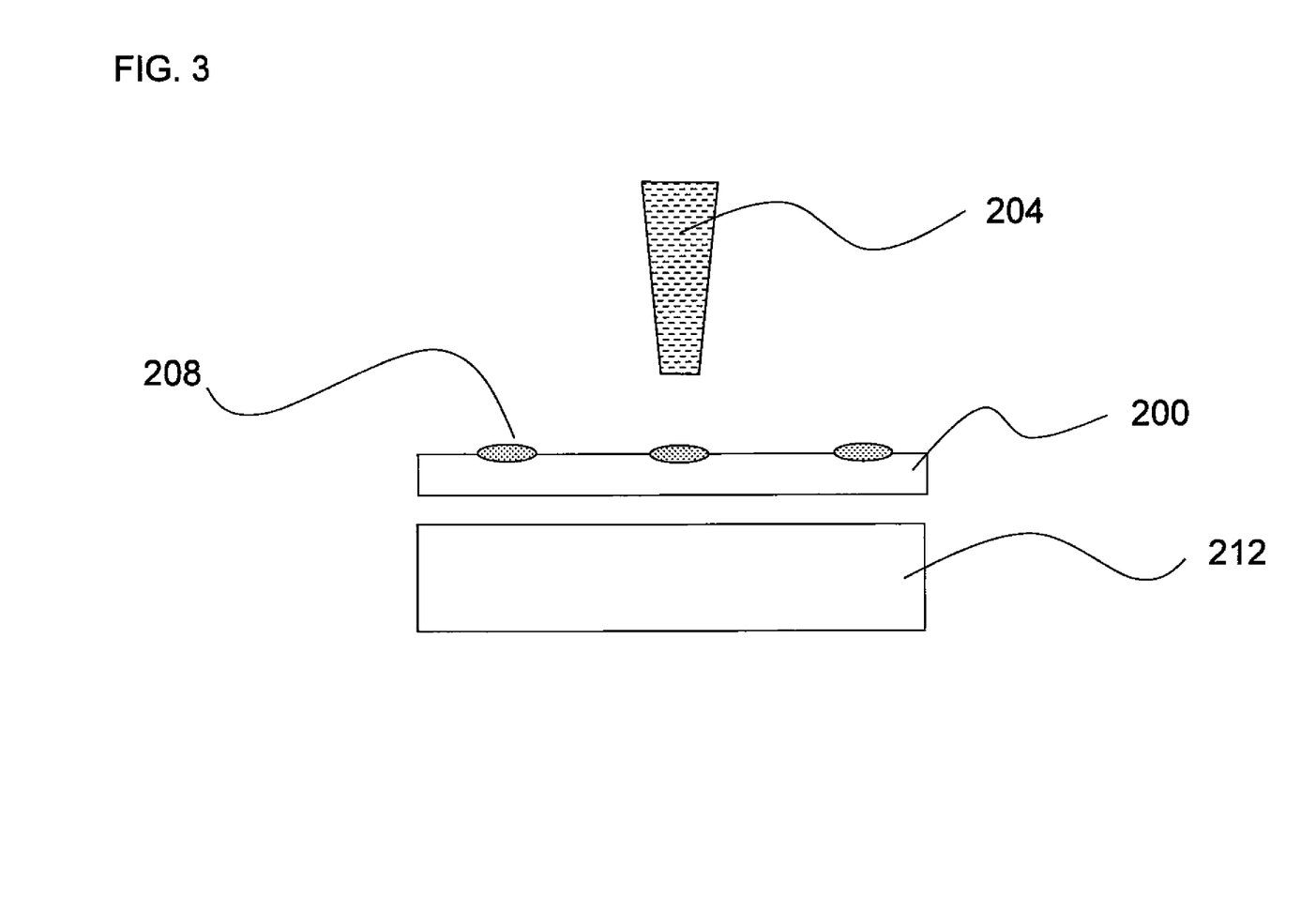
FIG. 3 depicts a side view of the embodiment of FIG. 2.
Figure 4:
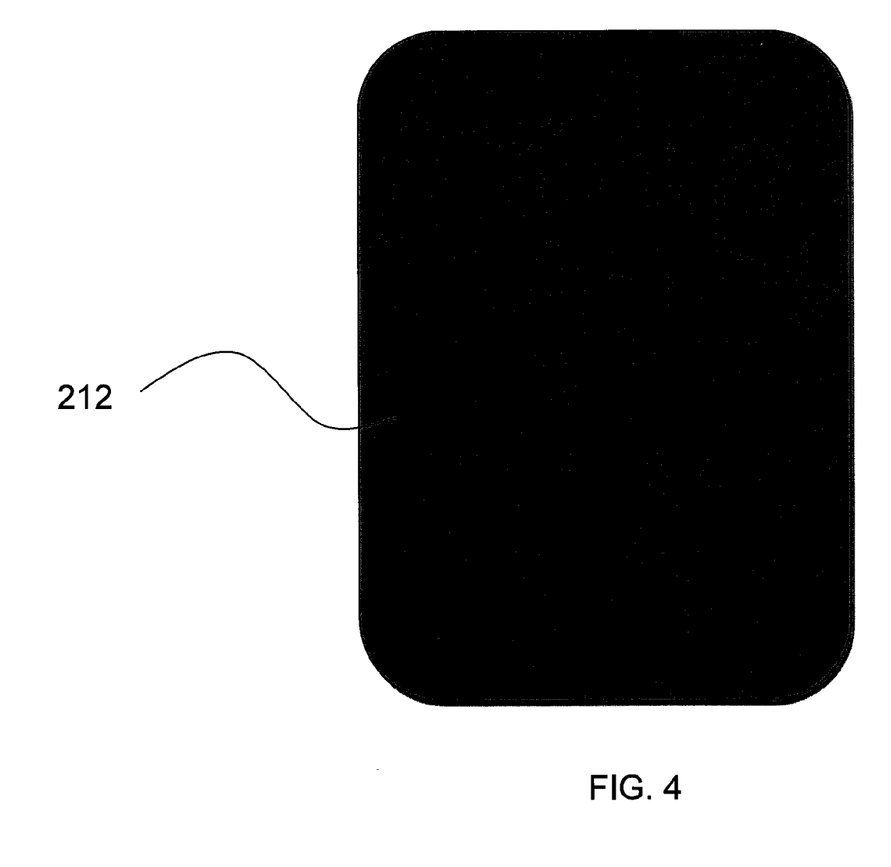
FIG. 4 displays a saturated loading sheet placed on top of a hydrogel sheet on a flat surface.

In some circumstances, however, the drug-loading solution will run off of the smooth surface of the hydrogel. Accordingly, in some embodiments, the unloaded hydrogel patch is loaded with the biologically active substance by employing the wicking capabilities of a nonwoven or woven fabric. The fabric, cut approximately to the size of the original non-loaded hydrogel, is placed on the surface of the hydrogel after the release liner is removed. Force is then applied to establish good contact between hydrogel and nonwoven fabric. See FIGS. 2-4. The drug solution may then be placed onto the surface of the nonwoven fabric 200 by dispenser, pipette, dropper, or other similar mechanism 204. The solution can be loaded onto the fabric 200 in a single dose as a bolus of solution or alternatively as a series of drops 208, as in FIG. 2. The main goal of these loading procedures is to obtain maximum coverage of the biologically active agent-containing solution within the nonwoven fabric. When employing these techniques, little or no drug loading solution leaks out of the fabric, but rather remains within the fabric to be absorbed by the hydrogel. After being placed onto the woven or nonwoven fabric, the drug solution is temporarily absorbed within the voids of the fabric. The biologically active agent subsequently diffuses into the hydrogel (FIG. 3, 212) where it dissolves to form a single phase with the hydrogel. In certain embodiments, the hydrogel is able to absorb a large volume of solutions with 500% by weight routinely observed. After sufficient time, the drug diffuses into the nonwoven fabric 200 and then uniformly into the hydrogel 212 as shown in FIG. 4. In other embodiments, the fabric is loaded with drug prior to contacting it with the hydrogel.

Certain configurations of hydrogel and nonwoven fabric that will form a uniform drug loaded product of acceptable physiological properties, content uniformity, and product uniformity include:

1. Nonwoven fabric is placed on top of dry non-loaded hydrogel. Drug solution added to the nonwoven fabric. Drug solution absorbs into hydrogel reservoir through the nonwoven fabric.
2. Nonwoven fabric is continuously laminated to non-loaded hydrogel. Laminate is cut to fit the size of the transdermal patch. Laminate is facing up and drug-containing solution is added. Drug solution absorbs into the hydrogel reservoir.
3. Nonwoven fabric is continuously laminated to non-loaded hydrogel. Laminate is cut to fit the size of the transdermal patch. Laminate is facing up drug-containing solution is added to the laminate. Laminate is then flipped over onto flat surface. Drug solution absorbs into the hydrogel reservoir.
4. The hydrogel reservoir is cut to the size of the final transdermal patch product. The nonwoven fabric is cut to the same size. Drug-containing solution is loaded into nonwoven fabric. The drug solution-loaded nonwoven fabric is placed on top of hydrogel. Drug-containing solution absorbs into the hydrogel from the nonwoven fabric.
5. The hydrogel reservoir is cut to the size of the final transdermal patch product. The nonwoven fabric is cut to the same size and is loaded with drug. The hydrogel is placed on top of the nonwoven fabric. The drug-containing solution imbibes from nonwoven into hydrogel.

Other alternative configurations include where the nonwoven fabric remains on the loaded hydrogel as a backing liner or where another liner replaces the nonwoven fabric. If an impermeable film is employed as the replacement liner, the patch may also possess occlusive properties.

Yet another alternative method for loading the hydrogel would include placing fabric on both sides of the hydrogel. Each piece of fabric would preferably be loaded with one-half of the total amount of loading solution. This configuration would accelerate the loading rate of drug into the hydrogel transdermal patch. From the configurations already specified the fabric pad or pads could be replaced by liners with at least one of the liners being releasable to allow for application of the transdermal patch to the skin of patients.

The present invention provides multiple benefits over the prior art. By crosslinking with ionizing radiation the hydrogel first and subsequently loading the biologically active agent, the present invention avoids any deleterious effects of the ionizing radiation on the biological active agent.

In an alternative embodiment, complete solubilization of the drug into the hydrogel reservoir need not occur prior to packaging for patient use. Instead, the hydrogel patch may be exposed to the biologically active agent through any of the mechanisms as described above. Before complete solubilization of the product has occurred, the transdermal patch may be placed and sealed in the final packaging. As the formulation is stored during shipping and prior to use by the patient, the drug will solubilize into the hydrogel. By the time the patient uses the transdermal patch, complete or near complete distribution of the biologically active agent into the hydrogel is accomplished.

The hydrogels of the present invention display excellent adherence to skin, while not requiring the use of any additional adhesive which may result in discomfort to the patient upon removal. The hydrogels of the present invention may also be combined with either an occlusive or non-occlusive backing material. The backing material provides support for the hydrogel and protects both during administration and from wear and tear while the hydrogel is on the patient's skin. The hydrogels of the present invention may also contain an integral scrim. For example in some embodiments, the transdermal patch may include a top (i.e., away from the application surface) liner of low density polyethylene having an approximate thickness of 2 mils and a bottom (i.e., covering the surface to be applied to that patient's skin) of low density polyethylene having an approximate thickness of 7 mils. The specific materials that comprise the top and bottom liners may be selected based on the properties of the drug being applied and may vary widely. In some embodiments, the portion of the hydrogel facing the skin may include a layer that controls the rate of release of the drug from the hydrogel reservoir. In this way, sustained-release transdermal patches based on the present invention may be generated.

The formulations of the present invention possess the further benefit of having increased storage stability after packaging. Stable shelf-life of the formulations of the present invention in excess of five years has been observed. The formulations of the present invention may be subject to sterilization processes using ethylene oxide while maintaining superior shelf-life stability. The hydrogels of the present invention may be packaged in a polypaper foil which would result in even greater stability.

Example 1

To investigate the release characteristics of the hydrogel transdermal patches of the present invention, the following experiment was conducted on three patch types. Lido-PG patches tested contained 5% lidocaine, 22% PVP K90, 27% PEG 300, 0.50% phenoxyethanol, 0.18% methylparaben, 0.05% propylparaben, and 50.27% de-ionized water. Lido-T patents tested contained 5% lidocaine, 24.82% transcutol, 0.08% methylparaben, 0.03% propylparaben, 0.24% phenoxyethanol, 35.21% water, 15.41% PVP, and 18.91% PEG. Lidoderm® is the commercially available formulation.

In vitro skin permeation experiments were conducted with Lidoderm®, Lido-T and Lido-PG patches, as defined above. Three replicates were used for all the patch types. The samples were assayed using high performance liquid chromatography (HPLC).

Human epidermis was separated from the split thickness skin by the heat separation method. In vitro skin permeation experiments were conducted using Franz-type vertical diffusion cells. Heat separated human cadaver epidermis was used as the membrane for all the permeation experiments. The skin was visually observed against light for any obvious defects prior to mounting in the cell. The following experimental conditions were used for the in vitro skin permeation experiments:
Cell Area: 1 $cm^2$
Receiver volume: 8 mL
Receiver solution: 20% propylene glycol/80% water mixture
Sample volume: 1.5 mL
Receiver temperature: 37° C.

Patches were cut to a size bigger than the cell area to ensure that the patch covered the whole area of the cell. Similarly the human epidermal membranes were cut ensuring that the skin covered the area of the cell completely. A saturated solution of lidocaine in ethanol was prepared by adding excess amount of the drug in a scintillation vial containing ethanol. It was ensured that excess solute was present for at least 12 h before use.

The receiver solution used was a solvent mixture containing 20% propylene glycol/80% water and was thermostated at 37° C. for the duration of the experiment. The sample volume was 1.5 mL and the sampling times were 0, 0.5 h, 1 h, 2 h, 4 h, 6 h, 8 h, 12 h and 24 h. The samples were assayed using HPLC.

All the three lidocaine patches showed typical permeation profiles. Lido-PG showed highest permeation rates compared to Lidoderm® and Lido-T. The cumulative amount of lidocaine permeated at the end of 12 h is presented in the Table below.

| Patch | Cumulative amount of lidocaine transported at the end of 12 hours (µg/$cm^2$) | Cumulative amount of lidocaine transported at the end of 12 hours (mg/140 $cm^2$) |
| --- | --- | --- |
| Lidoderm ® | 124 ± 2 | 17 |
| Lido-T | 133 ± 37 | 18 |
| Lido-PG | 432 ± 166 | 60 |
| Lidocaine in ethanol (saturated) | 143 ± 52 | — |

It can be seen from the table that approximately 60 mg would be delivered from a 140 $cm^2$ Lido-PG patch, which is significantly higher than both Lido-T and Lidoderm®. The latter two patches showed similar amounts delivered (18 and 17 mg respectively) at the end of 12 hours. The cumulative amount of lidocaine in ethanol was similar to the Lidoderm® and Lido-T. Thus, the hydrogel transdermal patches of the present invention that include propylene glycol display significantly better delivery of lidocaine to human skin than the commercially available Lidoderm® product.

Example 2

In example 2, post-loading of hydrogel sheet with lidocaine free base (CAS number 134-58-6) dissolved in solutions that can solubilize the drug and can be absorbed by the hydrogel while maintaining solubility of the drug and solvent down to 0° C. The patch considered is a 5% lidocaine free base hydrogel patch of 140 $cm^2$ area containing 700 mg of the active. The hydrogel used is a 25 mil thick and is radiation crosslinked composed of poly (vinylpyrolidone) K90/poly (ethylene glycol) PEG-300 manufactured by Aqua-Med Technologies Inc. One such solvent system is a solution of propylene glycol (PG) and Transcutol HP. Both solvents used were of compendial grade. The transcutol ranged from 0.00% to 100%. The specific solution used in this example is 90% PG and 10% Transcutol. The hydrogel sheet is cut to 10 cm×14 cm and the release liner is removed. The nonwoven is DuPont™ medical grade poly ethylenethphalate (PET) 8005 of basis weight 2 oz/$yd^2$. It is placed on the exposed surface of the hydrogel. The laminate was placed upon a balance and tared. Drug loading solution consisting of 16.69% lidocaine free base dissolved in a solvent mixture consisting of 10% by weight Transcutol, HP and 90% propylene glycol USP was added to the nonwoven by pipette to 4.19 g. The laminate containing the drug solution was promptly packaged and sat for 36 hours. The weight of each component was weighed separately. The laminate patch was then placed in a foil laminate package and promptly sealed. After 36 hours the laminate patch was weighed as well as the separate components the gel and nonwoven material. From the initial weights of these components, the amount of drug transferred to the gel was 651 mg or 93.1%.

What is claimed is:

1. A transdermal formulation for administering lidocaine to a patient in need thereof, comprising:
    a hydrogel, said hydrogel comprising a polymer-water mixture and transcutol, wherein said hydrogel is generated by exposing said polymer-water mixture to ionizing radiation; and
    lidocaine dispersed in said hydrogel.

2. The transdermal formulation of claim 1, wherein said transdermal formulation delivers two to four times more lidocaine to said patient over a twelve-hour period than LIDODERM®.

3. The transdermal formulation of claim 1, wherein said polymer is selected from the group consisting of polyethylene oxide, polyvinylpyrrolidone, polyethylene glycol, and mixtures thereof.

4. The transdermal formulation of claim 1, wherein said polymer-water mixture comprises from about 3% to about 60% polymer.

5. The transdermal formulation of claim 1, wherein said polymer-water mixture comprises from about 10% to about 90% water.

6. The transdermal formulation of claim 1, further comprising a water-retaining agent.

7. The transdermal formulation of claim 6, wherein said water-retaining agent is present at a concentration of about 1% to about 70%.

8. The transdermal formulation of claim 7, wherein said water-retaining agent is selected from the group consisting of glycols and saccharides.

9. The transdermal formulation of claim 8, wherein said water-retaining agent is ethylene glycol, diethylene glycol, polyethylene glycol, glycerin, sorbitol, martitol, propylene glycol, or 1,3-butylene glycol.

10. The transdermal formulation of claim 1, wherein said transdermal formulation has a pH from about 5.0 to about 7.8.

11. The transdermal formulation of claim 1, wherein said polymer-water mixture comprises about 22% polyvinylpyrrolidone, about 27% polyethylene glycol, and about 50% deionized water.

12. The transdermal formulation of claim 1, wherein said medicament is present at a concentration between about 0.5% and about 20%.

* * * * *